United States Patent [19]

Burvee

[11] Patent Number: 4,810,418

[45] Date of Patent: Mar. 7, 1989

[54] ELECTRICALLY CONDUCTIVE COMPOSITION

[75] Inventor: Richard W. Burvee, Austin, Tex.

[73] Assignee: Minnesota Mining and Manufacturing Company, St. Paul, Minn.

[21] Appl. No.: 29,339

[22] Filed: Mar. 23, 1987

[51] Int. Cl.$^4$ ............................................... H01B 1/00
[52] U.S. Cl. ..................................... 252/500; 252/518; 252/315.1; 252/315.4; 128/384; 128/388; 128/796; 128/799; 361/212; 361/220
[58] Field of Search .................. 252/500, 518, 315.01, 252/315.1, 315.4; 525/384, 418; 561/212, 220, 223, 224; 128/384, 385, 388, 796, 799, 798, 802, 804; 57/901; 174/5 R; 2/162, 170

[56] References Cited

U.S. PATENT DOCUMENTS

| | | | |
|---|---|---|---|
| 4,398,277 | 8/1983 | Christiansen et al. | 361/220 |
| 4,473,492 | 9/1984 | Schnolka | 252/518 |
| 4,554,924 | 11/1985 | Engel | 252/500 |
| 4,588,762 | 5/1986 | Mruh et al. | 252/500 |
| 4,692,273 | 9/1987 | Lawrence | 252/518 |

*Primary Examiner*—Josephine Barr
*Attorney, Agent, or Firm*—Donald M. Sell; Walter N. Kirn; James V. Lilly

[57] ABSTRACT

A substantially water and salt free electrically conductive composition used to assure good electrical conductivity between two points. The composition remains moist (i.e., it does not dry or harden) over an extended period of time.

14 Claims, No Drawings

ELECTRICALLY CONDUCTIVE COMPOSITION

BACKGROUND OF THE INVENTION

1. Technical Field

The invention relates to an electrically conductive composition.

2. Background Art

Electrically conductive compositions, such as gels, creams or jellies, have found utility in providing electrical connection between various locals. For example, it is customary for persons involved in the manufacture of integrated circuits and other sensitive electronic components to wear wrist straps that are electrically connected to ground to guard against the accumulation of electrostatic charges. U.S. Pat. No. 4,398,277 discloses one such wrist strap which comprises a fabric wrist band which holds an electrically conductive stainless steel plate against the wearer's wrist. A wire conductor provides an electrical path from the metal wrist plate to ground. Additionally, the fabric wrist band is electrically conductive due to the presence of silver-plated filaments in the fabric. These filaments provide a continuous electrical path from the wearer's wrist to ground even if the stainless steel plate accidentally moves out of contact with the wearer's wrist.

The use of a moisturizer, such as a skin lotion, is recommended to ensure good electrical contact between the wearer's body and the wrist strap, particularly in dry (e.g., low humidity) conditions. The use of moisturizers has, however, proven to be unreliable for this purpose as they tend to lose their skin-moistening effect upon evaporation of the water present in them. Additionally, both perspiration and moisturizers contain materials such as salts that can be corrosive to metals and which may, over a long period of time, gradually attack both the face of a stainless steel wrist plate and the silver plating of the filaments thereby reducing the electrical conductivity of the strap. Even a small reduction in electrical conductivity of the wrist strap is a major concern since the loss of conductivity could allow a sudden electrostatic discharge from the wearer to an electronic component being handled. Such a discharge could damage the component thereby either rendering it inoperative immediately or causing it to fail prematurely.

Electrically conductive compositions, such as gels, are in widespread medical use for ensuring good electrical contact between the skin and electrodes such as are used in EKG tests. These compositions generally comprise humectants, bactericides, thickeners, water and electrolytic salts which enhance electrical conductivity. The use of such salts is detrimental to the long term efficacy of the wrist strap due to the corrosive effect they would have on the metals in the strap. Moreover, the water present in such compositions tends to evaporate within a small fraction of a typical wearing time encountered in the manufacture of integrated circuits. This would require frequent reapplication of such compositions thereby magnifying the problems caused by the presence of the salts, and adding to the inconvenience in using the strap.

SUMMARY OF THE INVENTION

The present invention overcomes these disadvantages. It provides an electrically conductive composition which is substantially free from water and conductivity enhancers such as electrolytic salts. Consequently, the composition can be used to provide good electrical conductivity between a wrist strap and the wrist of a wearer. This is particularly surprising since the composition is substantially free from water and electrolytic salts. Furthermore, since it is substantially free from water it remains effective for extended periods of time.

In accordance with the present invention there is provided an electrically conductive composition which is substantially free from water and salts and which comprises a mixture of at least one polyhydric alcohol and at least one thickener. Substantially free from water means that the composition contains less than 10% by weight water. Substantially free from salts means that the composition contains less than 0.001% by weight of a salt which possess electrolytic capabilities (such as sodium or potassium chloride).

The present invention is not limited to use with wrist straps of the type described above, but may be employed wherever it is desired to establish a conductive path between two points via a conductive medium. For example, the composition of the invention may be used in the device disclosed in copending application Ser. No. 07/029,340, now U.S. Pat. No. 4,762,497 filed 3-23-87. The device of that application has two plastic parts, one of which is formed with a reservoir for an electrically conductive composition such as a gel. When the two parts are interconnected to entrap a fabric such as the sleeve of a cleanroom garment, the gel is squeezed through the fabric to complete an electrical path between an electrode in each of the parts, thus completing an electrical connection between a wrist strap and ground. In such use, the gel remains viable as long as the connector entraps the fabric. Upon removing the connector, the gel is easily cleaned out of the reservoir, permitting the connector to be reused. The gel may also be easily cleaned from the garment leaving it uncontaminated for the next use.

DETAILED DESCRIPTION

The principal components of the present invention, that is the polyhydric alcohol and thickener, may be combined in a wide variety of concentration ratios. Preferably the thickener is present at a level of at least 1 part by weight per 100 parts by weight polyhydric alcohol. While the upper level of thickener employed is not critical, it preferably comprises no more than about 10 parts by weight per 100 parts by weight of the alcohol. At substantially higher levels, the composition becomes too viscous to conveniently handle. More preferably the thickener comprises from about 3 to 7 parts by weight per 100 parts by weight polyhydric alcohol.

The composition of the invention has an electrical volume resistivity of less than $5 \times 10^6$ ohm-cm (preferably less than $1 \times 10^5$ ohm-cm). It is understood that as resistivity decreases, conductivity increases.

Volume resistivity of the composition may be determined by immersing two circular electrodes (each 0.45 cm² in area) in the composition such that they are about 0.5 cm apart from center point to center point. It is not necessary that the spacing between the electrodes be exactly 0.5 cm. However, it is necessary that the exact spacing be known. While immersed, a 5 volt potential is applied across the electrodes and the electrical resistance is measured. The volume resistivity ($R_v$) is then determined from the equation $$R_v = (A/T) \times R_m$$

where A is the area of one of the electrodes, T is the distance between the electrodes, and $R_m$ is the measured resistance.

The composition of the invention preferably has a pH of 7 or less. While compositions of higher pH are within the scope of the invention it has been found that a bacteriacide and/or mold inhibitor is often required to prevent the growth of unwanted organisms. Typically from 0.01 to 0.1 part by weight of the bacteriacide and/or mold inhibitor per 100 parts by weight of the polyhydric alcohol is sufficient to prevent unwanted growth.

While the lower pH limit is not critical, it is preferred that it not be below 3. Below 3 the acidity of the composition may have a negative effect on long term use. Additionally, the composition is less viscous (i.e., more fluid) at lower pH values. This may cause minor problems during use. However, it is noted that the pH of the composition may be increased through the addition of a minor amount of a basic material such as triethanol amine thereby causing the composition to become less fluid. Preferably the composition has a pH of from 4 to 7 and more preferably a pH of from 4 to 6.

Polyhydric alcohols useful in the present invention are those compounds or polymers having more than one hydroxyl group. Preferably the polyhydric alcohol is water soluble and normally liquid at room temperature (e.g., 20° C.). When polyhydric alcohols which are not normally liquid at room temperature are employed in the composition of the invention, they should be mixed with one or more liquid polhydric alcohols. Examples of useful polyhydric alcohols are ethylene glycol, propylene glycol, 1,2,4 butane triol, polyethyleneoxide (e.g., Carbowax TM 400) and the like. Glycerol may also be used as a polyhydric alcohol in the present invention, although a second polyhydric alcohol may have to be added in order to achieve the desired electrical conductivity. Those skilled in the art will, of course, recognize that ethylene glycol may cause some dermal reactions.

Thickeners useful in the present invention are materials which cause the polyhydric alcohol to increase in viscosity. Examples of useful thickeners include polymers containing acid anhydride units. These polymers are molecules built up by the repetition of a sufficient number of small chemical units wherein it is preferred that at least 2 mole % of the units contain an acid anhydride group.

A particularly preferred acid anhydride-containing polymer comprises the polymerization product of an addition-polymerizable acid anhydride (such as acetic anhydride, maleic anhydride and the like) with an olefinic, addition-polymerizable monomer free from the anhydride functionality such as acrylate esters (e.g., methyl acrylate, methyl methacrylate, butyl acrylate, etc.); vinyl ethers (e.g., methyl vinyl ether, 2-ethyl hexyl vinyl ether, decyl vinyl ether); vinyl acrylates (e.g., vinyl acetate, vinyl butyrate, etc.); olefins (e.g., ethylene, propylene, styrene, α-methyl styrene, isobutylene, etc.); olefinic polycarboxylic acid esters (e.g., dimethyl maleate, dimethyl fumurate, etc.; and vinyl halides (e.g., vinyl chloride, vinylidene dichloride).

Other ingredients may be used in the composition of the invention to accomplish a desired result. For example, as noted previously, bacteriacides and/or mold inhibitors may be employed. Ingredients to adjust the pH of the final product may be employed. Typically these other ingredients are employed at minor levels, that is, up to 0.1 parts by weight per 100 parts by weight polyhydric alcohol.

The composition of the invention may be easily prepared by combining the polyhydric alcohol, thickener and any optional ingredients in a suitable vessel and mixing in the presence of heat (e.g., 80° C. to 100° C.) until the composition begins to thicken, typically from 1 to 4 hours. The pH of the initial combination of ingredients may preferably be adjusted to about 7 by the addition of a minor amount of triethanol amine or the like. Once the composition has thickened its pH generally goes to a value of 5 or less. After thickening, the composition is cooled to room temperature.

EXAMPLE

A mixture of 51 grams of ethylene glycol, 16 grams of glycerol, 2 grams of a medium molecular weight copolymer of approximately equal parts of methyl vinyl ether and maleic anhydride (Gantrez TM 139 from GAF, Inc., weight average molecular weight of 138), and six drops (approximately 0.4 gm) of triethanol amine was heated to 85° C. with stirring until gelling had started. This temperature was maintained for 3 hours to provide a gel which then was allowed to cool to room temperature. The pH of the gel was 4.5 and its electrical resistivity was $2.4 \times 10^5$ ohm-cm, surprisingly good in view of it being water-free and salt-free.

This electrically conductive gel was spread onto the wrists of a number of persons, who then wore a wrist strap of the type disclosed in U.S. Pat. No. 4,398,277. Testing indicated that in each case, the electrical conductivity between the body of the wearer and the wrist strap was adequate, both immediately upon applying the wrist strap and after the wrist strap had been worn continuously for about eight hours.

Using a syringe, this electrically conductive gel was used in a connector having two plastic parts each having an electrode in the base. The gel was squirted into the cavity of a tube of elastic, polymeric, electrically conductive, open-cell foam which was formed with a cavity that was open at both ends. The cavity was 0.32 cm in diameter and 0.96 cm in length. The gel-filled tube was inserted into one of the plastic parts. The other plastic part was interconnected to the first to entrap a piece of a cleanroom garment fabric (polyester) which had a thickness of about 0.125 mm, compress the foam tube and transmit a squeezing force against the electrically conductive gel to force it to flow into the interstices of the fabric and into contact with the flat electrode of the other plastic part. The electrical resistance between the electrodes (each 1.0 cm in diameter) was measured to be 0.2 megohm. In order to bleed off static charges, the electrical resistance should be about one megohm or less.

I claim:

1. An electrically conductive composition which contains less than 10% by weight water and less than 0.001% by weight salt and which comprises a mixture of at least one polyhydric alcohol selected from the group consisting of propylene glycol, ethylene glycol, glycerol, 1,2,4 butane triol, and polyethylene glycol and at least 1 part by weight per 100 parts by weight of said alcohol of a thickener selected from the group consisting of polymers having at least 2 mole % of said acid anhydride units, wherein said thickener results from the polymerization of an addition polymerizable acid anhydride and an olefinic, addition polymerizable monomer free from anhydride functionality, wherein said addition polymerizable acid anhydride is selected from th group consisting of actice anhydride and maleic anhydride and said olefinic, addition polymerizable monomer is selected from acrylate esters, vinyl ethers, vinyl acrylates, olefins, olefinic polycarboxylic acid esters, and vinyl halides.

2. A composition according to claim 1 having an electrical resistivity of less than $5 \times 10^6$ ohm-cm.

3. A composition according to claim 2 having a pH in the range of from 3 to 7.

4. A composition according to claim 3 containing at most 10 parts by weight of said thickener per 100 parts by weight of said polyhydric alcohol.

5. A composition according to claim 2 wherein said polyhydric alcohol is normally liquid at 20° C.

6. A composition according to claim 5 wherein said polyhydric alcohol is selected from the group consisting of ethylene glycol and propylene glycol.

7. A composition according to claim 6 wherein said polyhydric alcohol is ethylene glycol.

8. A composition according to claim 6 wherein said polyhydric alcohol is propylene glycol.

9. A composition according to claim 1 wherein said addition polymerizable acid anhydride is maleic anhydride and said olefinic, addition polymerizable monomer is a vinyl ether.

10. A composition according to claim 9 wherein said thickener comprises a copolymer of approximately equal parts of said vinyl ether and said maleic anhydride.

11. A composition according to claim 10 wherein said vinyl ether is a methyl vinyl ether.

12. An electrically conductive composition ccording to claim 1 which has an electrical resistivity of less than $5 \times 10^6$ ohm-cm and a pH of from 3 to 7.

13. A gel according to claim 1.

14. A non-drying gel according to claim 1.

* * * * *

UNITED STATES PATENT AND TRADEMARK OFFICE
CERTIFICATE OF CORRECTION

PATENT NO. : 4,810,418

DATED : MARCH 7, 1989

INVENTOR(S) : Richard W. Burvee

It is certified that error appears in the above-identified patent and that said Letters Patent is hereby corrected as shown below:

Col. 3, line 34-35, "polyethyleneoxide" should be -- polyethylene glycol --.

Col. 5, line 3, "th" should be -- the --.

Col. 6, line 15, "ccording" should read -- according --.

Signed and Sealed this

First Day of August, 1989

Attest:

Attesting Officer

DONALD J. QUIGG

Commissioner of Patents and Trademarks